(12) United States Patent
Wätjen

(10) Patent No.: US 7,560,562 B2
(45) Date of Patent: Jul. 14, 2009

(54) PIPERIDINE DERIVATIVES AND THEIR USE AS MONOAMINE NEUROTRANSMITTER RE-UPTAKE INHIBITORS

(75) Inventor: Frank Wätjen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 552 days.

(21) Appl. No.: 10/530,012

(22) PCT Filed: Oct. 30, 2003

(86) PCT No.: PCT/DK03/00734

§ 371 (c)(1),
(2), (4) Date: Apr. 1, 2005

(87) PCT Pub. No.: WO2004/039778

PCT Pub. Date: May 13, 2004

(65) Prior Publication Data

US 2006/0094759 A1    May 4, 2006

Related U.S. Application Data

(60) Provisional application No. 60/469,817, filed on May 13, 2003.

(30) Foreign Application Priority Data

Nov. 1, 2002   (DK) ................. 2002 01689
May 13, 2003  (DK) ................. 2003 00727

(51) Int. Cl.
C07D 211/20   (2006.01)
A61K 31/445   (2006.01)

(52) U.S. Cl. ..................... 546/236; 514/317

(58) Field of Classification Search ............ 514/317; 546/236

See application file for complete search history.

(56) References Cited

U.S. PATENT DOCUMENTS

3,912,743 A * 10/1975 Christensen et al. ......... 546/197
4,485,109 A * 11/1984 Ciganek ...................... 514/317
6,180,648 B1 * 1/2001 Kozikowski et al. ......... 514/317
6,376,673 B1 * 4/2002 Moldt et al. ................. 546/229
6,440,996 B1 * 8/2002 Kozikowski et al. ......... 514/316

FOREIGN PATENT DOCUMENTS

EP       190496      *  8/1986
WO    WO-98/51668 A    11/1998
WO    WO-00/20390 A     4/2000

OTHER PUBLICATIONS

Akunne et al. "MPTO leasions . . . " Neurochem. Res. v.17(3) p. 261-264 (1992).*
Kung et al. "Characterization of . . . " Europ. J. Muclear Med. v.26(8) p. 844-853 (1999).*
Christensen et al. "Antidepressant . . . " CA 81:152011 (1974).*
Akunne et al. "3H-1-2(2-thienyl)cyclohexyl piperidine . . . " CA 115:223268 (1991).*
Kuroita et al. "Preparation of cinnamamides . . . " CA 132:236993 (2000).*
Christensen et al. CA81:152011 (1974) RN 54087-81-9.*
Moldt et al. Ca 130:13920 (1998) RN 216009-52-8.*
Waetjen CA 140:406740 (2004).*
Kugaya et al. "Changes in human in vivo serotonin . . . " Neuropsychopharm. v.28, p. 413-420 (2003).*
Petukhov et al.: SAR studies of piperidine-based analogues of cocaine. 4. Effect of N-Modification and ester replacement; J. Med. Chem. 2002 vol. 45 No. 15, pp. 3161-3170.

* cited by examiner

*Primary Examiner*—Celia Chang
(74) *Attorney, Agent, or Firm*—Birch, Stewart, Kolasch & Birch, LLP

(57) ABSTRACT

This invention relates to novel piperidine derivatives useful as monoamine neurotransmitter re-uptake inhibitors.

In other aspects the invention relates to the use of these compounds in a method for therapy and to pharmaceutical compositions comprising the compounds of the invention.

8 Claims, No Drawings

PIPERIDINE DERIVATIVES AND THEIR USE AS MONOAMINE NEUROTRANSMITTER RE-UPTAKE INHIBITORS

This National Phase PCT application claims priority under 35 U.S.C. 119(e) on U.S. Provisional Application No(s). 60/469,817 filed on May 13, 2003 and under 35 U.S.C. 119(a) on Patent Application No(s). PA 2002 01689 & PA 2003 00727 filed in Denmark on Nov. 1, 2002 & May 13, 2003; respectively, all of which are hereby incorporated by reference.

TECHNICAL FIELD

This invention relates to novel piperidine derivatives useful as monoamine neurotransmitter re-uptake inhibitors.

In other aspects the invention relates to the use of these compounds in a method for therapy and to pharmaceutical compositions comprising the compounds of the invention.

BACKGROUND ART

Petukhov et al. [Petukhov P A, Zhang J, Kozikowski A P, Wang C Z, Ye Y P, Johnson K M and Tella S R]; *J. Med. Chem.* 2002 45 3161-3170] describe SAR studies of piperidine-based analogues of cocaine.

WO 00/20390 (Georgetown University) describes monomeric and dimeric heterocycles and therapeutic uses thereof.

WO 98/51668 (NeuroSearch A/S) describes 3-alkoxyimidomethyl-piperidine derivatives active as neurotransmitter re-uptake inhibitors. Examples 1 and 2 describe two intermediate mixtures, (±)-cis/trans-1-methyl-3-methoxycarbonyl-4-(3,4-dichlorophenyl)-piperidine and (±)-cis/trans-1-methyl-3-hydroxymethyl-4-(3,4-dichlorophenyl)-piperidine. No pharmacological use of these two intermediate mixtures is disclosed.

However, there is a continued strong need to find compounds with an optimised biochemical profile as regards the activity on reuptake of the monoamine neurotransmitters serotonin, dopamine and noradrenaline, such as the ratio of the serotonin reuptake versus the noradrenaline and dopamine activity.

Furthermore, there is a strong need to find effective compounds, which structurally and synthetically wise are unrelated to cocaine.

SUMMARY OF THE INVENTION

In its first aspect, the invention provides a piperidine derivative of the Formula I:

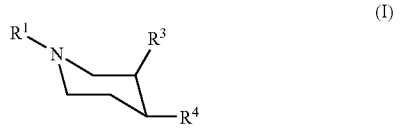

or any of its isomers or any mixture of its isomers, or a pharmaceutically acceptable salt thereof, wherein $R^1$, $R^3$ and $R^4$ are as defined below.

In its second aspect, the invention provides a pharmaceutical composition, comprising a therapeutically effective amount of a compound of the invention, or any of its isomers or any mixture of its isomers, or a pharmaceutically acceptable salt thereof, together with at least one pharmaceutically acceptable carrier, excipient or diluent.

In a further aspect, the invention provides the use of a compound of the invention, or any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to inhibition of monoamine neurotransmitter re-uptake in the central nervous system.

In a still further aspect, the invention relates to a method for treatment, prevention or alleviation of a disease or a disorder or a condition of a living animal body, including a human, which disorder, disease or condition is responsive to responsive to inhibition of monoamine neurotransmitter re-uptake in the central nervous system, which method comprises the step of administering to such a living animal body in need thereof a therapeutically effective amount of a compound of the invention, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Piperidine Derivatives

In its first aspect the present invention provides a piperidine derivative of formula I:

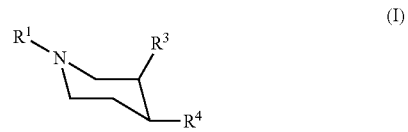

or any of its isomers or any mixture of its isomers, or a pharmaceutically acceptable salt thereof, wherein $R^1$ represents hydrogen, alkyl, alkenyl, alkynyl, cycloalkyl, cycloalkylalkyl or 2-hydroxyethyl;

$R^3$ represents —C(=O)—O—$R^c$ or —CH$_2$—O—$R^c$;

wherein $R^c$ represents hydrogen, alkyl, alkenyl, alkynyl, cycloalkyl or cycloalkylalkyl; $R^4$ represents

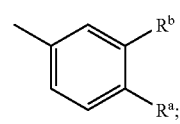

wherein $R^a$ and $R^b$ independently of each other represents halo or trifluoromethyl;

with the proviso that the mixture of isomers is not (±)-cis/trans-1-methyl-3-methoxycarbonyl-4-(3,4-dichlorophenyl)-piperidine or (±)-cis/trans-1-methyl-3-hydroxymethyl-4-(3,4-dichlorophenyl)-piperidine.

In one embodiment, $R^1$ represents hydrogen or alkyl.

In a second embodiment, $R^a$ and $R^b$ independently of each other represents halo. In a special embodiment, $R^a$ represents chloro. In a further embodiment, $R^b$ represents chloro. In a still further embodiment, $R^a$ represents chloro and $R^b$ represents chloro.

In a further embodiment, $R^3$ represents —C(=O)—O—$R^c$. In a further embodiment, $R^3$ represents —CH$_2$—O—$R^c$.

In a still further embodiment, $R^c$ represents hydrogen, alkyl or cycloalkylalkyl. In a further embodiment, $R^c$ represents hydrogen or alkyl. In a still further embodiment, $R^c$ represents alkyl or cycloalkylalkyl. In a special embodiment, $R^c$ represents hydrogen. In a further embodiment, $R^c$ represents alkyl, such as methyl or ethyl. In a still further embodiment, $R^c$ represents cycloalkylalkyl, such as cyclopropylmethyl.

In a further embodiment of the compound of formula I,
$R^1$ represents hydrogen, alkyl or cycloalkylalkyl;
$R^c$ represents hydrogen or alkyl; and
$R^a$ and $R^b$ independently of each other represent halo.

In a still further embodiment of the compound of formula I,
$R^1$ represents hydrogen or alkyl;
$R^c$ represents hydrogen or alkyl; and
$R^a$ and $R^b$ independently of each other represent halo.

In a further embodiment of the compound of formula I,
$R^1$ represents hydrogen or alkyl;
$R^3$ represents —CH$_2$—O—$R^c$;
$R^c$ represents alkyl or cycloalkylalkyl; and
$R^a$ and $R^b$ independently of each other represent halo.

In a special embodiment the chemical compound of the invention is
1-methyl-4-(3,4-dichlorophenyl)-piperidine-3-carboxylic acid methyl ester;
1-methyl-3-hydroxymethyl-4-(3,4-dichlorophenyl)-piperidine;
1-methyl-3-ethoxymethyl-4-(3,4-dichlorophenyl)-piperidine;
1-methyl-3-methoxymethyl-4-(3,4-dichlorophenyl)-piperidine;
1-methyl-3-cyclopropylmethoxymethyl-4-(3,4-dichlorophenyl)-piperidine;
1-methyl-3-isobutoxymethyl-4-(3,4-dichlorophenyl)-piperidine;
3-ethoxymethyl-4-(3,4-dichlorophenyl)-piperidine;
3-methoxymethyl-4-(3,4-dichlorophenyl)-piperidine;
3-cyclopropylmethoxymethyl-4-(3,4-dichlorophenyl)-piperidine;

or any of its isomers or any mixture of its isomers, or a pharmaceutically acceptable salt thereof.

In a further special embodiment the chemical compound of the invention is
(±)-Cis-1-methyl-4-(3,4-dichlorophenyl)-piperidine-3-carboxylic acid methyl ester;
(±)-Trans-1-methyl-4-(3,4-dichlorophenyl)-piperidine-3-carboxylic acid methyl ester;
(±)-Cis-1-methyl-3-hydroxymethyl-4-(3,4-dichlorophenyl)-piperidine;
(±)-Trans-1-methyl-3-hydroxymethyl-4-(3,4-dichlorophenyl)-piperidine;
(+)-Cis-1-methyl-3-hydroxymethyl-4-(3,4-dichlorophenyl)-piperidine;
(−)-Cis-1-methyl-3-hydroxymethyl-4-(3,4-dichlorophenyl)-piperidine;
(+)-Trans-1-methyl-3-hydroxymethyl-4-(3,4-dichlorophenyl)-piperidine
(−)-Trans-1-methyl-3-hydroxymethyl-4-(3,4-dichlorophenyl)-piperidine;
(±)-Cis-1-methyl-3-ethoxymethyl-4-(3,4-dichlorophenyl)-piperidine;
(±)-Cis-1-methyl-3-methoxymethyl-4-(3,4-dichlorophenyl)-piperidine;
(±)-Trans-1-methyl-3-ethoxymethyl-4-(3,4-dichlorophenyl)-piperidine;
(±)-Trans-1-methyl-3-methoxymethyl-4-(3,4-dichlorophenyl)-piperidine;
(+)-Cis-1-methyl-3-ethoxymethyl-4-(3,4-dichlorophenyl)-piperidine;
(+)-Cis-1-methyl-3-methoxymethyl-4-(3,4-dichlorophenyl)-piperidine;
(−)-Cis-1-methyl-3-methoxymethyl-4-(3,4-dichlorophenyl)-piperidine;
(+)-Cis-1-methyl-3-cyclopropylmethoxymethyl-4-(3,4-dichlorophenyl)-piperidine;
(−)-Cis-1-methyl-3-cyclopropylmethoxymethyl-4-(3,4-dichlorophenyl)-piperidine;
(−)-Cis-1-methyl-3-isobutoxymethyl-4-(3,4-dichlorophenyl)-piperidine;
(+)-Trans-1-methyl-3-ethoxymethyl-4-(3,4-dichlorophenyl)-piperidine;
(−)-Trans-1-methyl-3-ethoxymethyl-4-(3,4-dichlorophenyl)-piperidine;
(+)-Trans-1-methyl-3-methoxymethyl-4-(3,4-dichlorophenyl)-piperidine;
(−)-Trans-1-methyl-3-methoxymethyl-4-(3,4-dichlorophenyl)-piperidine;
(−)-Trans-1-methyl-3-cyclopropylmethoxymethyl-4-(3,4-dichlorophenyl)-piperidine;
(−)-Trans-1-methyl-3-isobutoxymethyl-4-(3,4-dichlorophenyl)-piperidine;
(+)-Cis-1-methyl-3-isobutoxymethyl-4-(3,4-dichlorophenyl)-piperidine;
(+)-Trans-1-methyl-3-isobutoxymethyl-4-(3,4-dichlorophenyl)-piperidine;
(+)-Trans-1-methyl-3-cyclopropylmethoxymethyl-4-(3,4-dichlorophenyl)-piperidine;
(−)-Cis-1-methyl-3-ethoxymethyl-4-(3,4-dichlorophenyl)-piperidine;
(+)-Cis-3-ethoxymethyl-4-(3,4-dichlorophenyl)-piperidine;
(−)-Cis-3-ethoxymethyl-4-(3,4-dichlorophenyl)-piperidine;
(+)-Cis-3-methoxymethyl-4-(3,4-dichlorophenyl)-piperidine;
(−)-Cis-3-methoxymethyl-4-(3,4-dichlorophenyl)-piperidine;
(+)-Cis-3-cyclopropylmethoxymethyl-4-(3,4-dichlorophenyl)-piperidine;
(−)-Cis-3-cyclopropylmethoxymethyl-4-(3,4-dichlorophenyl)-piperidine;
(+)-Trans-3-ethoxymethyl-4-(3,4-dichlorophenyl)-piperidine;
(−)-Trans-3-ethoxymethyl-4-(3,4-dichlorophenyl)-piperidine;
(+)-Trans-3-methoxymethyl-4-(3,4-dichlorophenyl)-piperidine;
(−)-Trans-3-methoxymethyl-4-(3,4-dichlorophenyl)-piperidine;
(−)-Trans-3-cyclopropylmethoxymethyl-4-(3,4-dichlorophenyl)-piperidine;
(+)-Trans-3-cyclopropylmethoxymethyl-4-(3,4-dichlorophenyl)-piperidine;
(+)-Cis-3-isobutoxymethyl-4-(3,4-dichlorophenyl)-piperidine;
(−)-Cis-3-isobutoxymethyl-(3,4-dichlorophenyl)-piperidine;
(+)-Trans-3-isobutoxymethyl-4-(3,4-dichlorophenyl)-piperidine;

(−)-Trans-3-isobutoxymethyl-4-(3,4-dichlorophenyl)-piperidine;

or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4- or 5-hexenyl, or 1,3-hexdienyl, or 1,3,5-hextrienyl.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic add, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic add, the citrate derived from citric add, the embonate derived from embonic add, the enantate derived from enanthic acid, the fumarate derived from fumaric acid, the glutamate derived from glutamic acid, the glycolate derived from glycolic add, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphthalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical compounds of the present invention may exist as enantiomers in (+) and (−) forms as well as in racemic forms (±). The racemates of these isomers and the individual isomers themselves are within the scope of the present invention.

Racemic forms can be resolved into the optical antipodes by known methods and techniques. One way of separating the isomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Furthermore, the compounds of the present invention may exist in cis or trans configurations as well as in mixtures thereof. The substituent $R^3$ and the substituent $R^4$ of the piperidine skeleton of formula I may in particular be in cis or trans configuration relative to each another. In one embodiment of the invention the substituents $R^3$ and $R^4$ are in trans configuration. In another embodiment of the invention the substituents $R^3$ and $R^4$ are in cis configuration. The invention includes all such isomers and any mixtures thereof including racemic mixtures.

Labelled Compounds

The compounds of the invention may be used in their labelled or unlabelled form. In the context of this invention "label" stands for the binding of a marker to the compound of interest that will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2H$ (deuterium), $^3H$ (tritium), $^{13}C$, $^{14}C$, $^{131}I$, $^{125}I$, $^{123}I$, and $^{18}F$.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

Compounds of the invention may be tested for their ability to inhibit reuptake of the monoamines dopamine, noradrenaline and serotonin in synaptosomes eg such as described in WO 97/30997.

Thus in a further aspect, based on the balanced activity observed in these tests, the compounds of the invention are considered useful in the treatment the treatment, prevention or alleviation of a disease or a disorder or a condition of a mammal, including a human, which disease, disorder or condition is responsive to inhibition of monoamine neurotransmitter re-uptake in the central nervous system.

In a special embodiment, the compounds of the invention are considered useful for the treatment, prevention or alleviation of mood disorder, depression, atypical depression, major depressive disorder, dysthymic disorder, bipolar disorder, bipolar I disorder, bipolar II disorder, cyclothymic disorder, mood disorder due to a general medical condition, substance-induced mood disorder, pseudodementia, Ganser's syndrome, obsessive compulsive disorder, panic disorder, panic disorder without agoraphobia, panic disorder with agoraphobia, agoraphobia without history of panic disorder, panic attack, memory deficits, memory loss, attention deficit hyperactivity disorder, obesity, anxiety, generalized anxiety disorder, eating disorder, Parkinson's disease, parkinsonism, dementia, dementia of ageing, senile dementia, Alzheimer's disease, acquired immunodeficiency syndrome dementia complex, memory dysfunction in ageing, social phobia, post-traumatic stress disorder, acute stress disorder, drug addiction, drug misuse, cocaine abuse, nicotine abuse, tobacco abuse, alcohol addiction, alcoholism, pain, inflammatory pain, neuropathic pan, migraine pain, tension-type headache, chronic tension-type headache, pain associated with depression, fibromyalgia, arthritis, osteoarthritis, rheumatoid arthritis, back pain, cancer pain, irritable bowel pain, irritable bowel syndrome, post-operative pain, post-stroke pain, drug-induced neuropathy, diabetic neuropathy, sympathetically-maintained pain, trigeminal neuralgia, dental pain, myofacial pain, phantom-limb pain, bulimia, premenstrual syndrome, late luteal phase syndrome, post-traumatic syndrome, chronic fatigue syndrome, urinary incontinence, stress incontinence, urge incontinence, nocturnal incontinence, premature ejaculation, erectile difficulty, anorexia nervosa, sleep disorders, autism, mutism, trichotillomania, narcolepsy, post-stroke depression, stroke-induced brain damage, stroke-induced neuronal damage or Gilles de la Tourettes disease. In a preferred embodiment, the compounds are considered useful for the treatment, prevention or alleviation of depression.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of monoamine neurotransmitter re-uptake in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

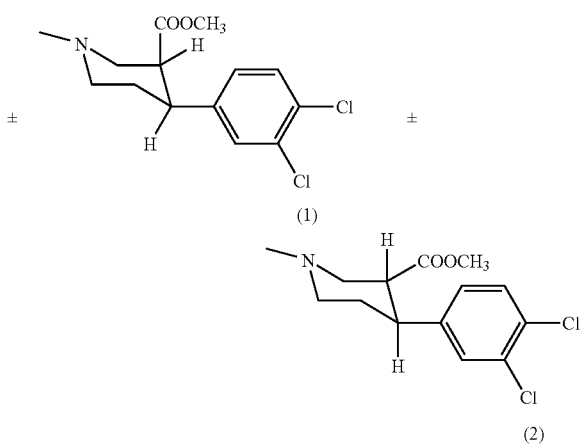

(±)-Cis-1-methyl-4-(3,4-dichlorophenyl)-piperidine-3-carboxylic acid methyl ester (1) and (±)-Trans-1-methyl-4-(3,4-dichlorophenyl)-piperidine-3-carboxylic acid methyl ester (2)

A stirred suspension of magnesium turnings (3.4 g, 142 mmol) in diethyl ether (20 ml) was added a solution of 1-bromo-3,4-dichlorobenzene (29 g, 130 mmol) in diethyl ether (150 ml). The mixture was heated at reflux for 20 minutes and then cooled at −40° C. A solution of arecoline (10 g, 65 mmol) in toluene (100 ml) was added slowly while keeping the internal temperature between −40° C. and −30° C. The reaction mixture was stirred at −20° C. for 6 hours and then added 4 N HCl (50 ml). The phases were then separated and the aqueous phase was added ammonia (aq) until basic pH and extracted with dichloromethane (4×100 ml), dried with magnesium sulfate and evaporated to an oil. The isomers (1)

and (2) were separated by column chromatography (petroleum ether, ether, triethylamine 70:25:5) to give 5.0 g (25%) of (1) (mp. 70-75° C.) and 2.0 g (10%) of (2) (oil).

Example 2

Method A1

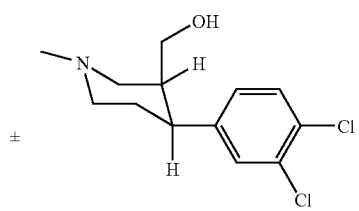

(±)-Cis-1-methyl-3-hydroxymethyl-4-(3,4-dichlorophenyl)-piperidine (3)

A solution of (1) (5.0 g, 17 mmol) in tetrahydrofuran (50 ml) at −50° C. was added LiAlH$_4$ (0.50 g, 13 mmol). Stirred at −30° C. for three hours, then quenched by addition of water and evaporated to a solid. The residue was dissolved in dichloromethane, dried with magnesium sulfate and evaporated to dryness. Yield 4.6 g of (3) (100%). Mp. 127-129° C.

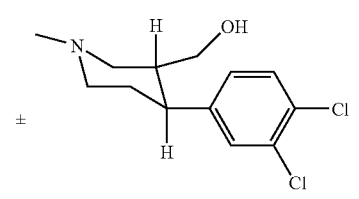

(±)-Trans-1-methyl-3-hydroxymethyl-4-(3,4-dichlorophenyl)-piperidine (4)

A solution of (2) (2.0 g, 6.6 mmol) was reduced according to method (A1) giving 1.9 g (100%) of product (4). Mp. 109-111° C.

Procedure (a)

The racemate can be separated into the individual enantiomers by precipitation of the mandelate salts.

(±)-Cis-1-methyl-3-hydroxymethyl-4-(3,4-dichlorophenyl)-piperidine (5)

A mixture of (3) (23.8 g, 86.8 mmol) and (−) mandelic acid (6.6 g, 43.4 mmol) in absolute ethanol (60 ml) was heated until clear solution. The reaction mixture was evaporated to dryness and recrystallized once from toluene (100 ml) and once from toluene (100 ml) and absolute ethanol (12 ml). The precipitate was isolated and purred into water (75 ml). Concentrated ammonia (aq) was added until basic pH and the mixture was extracted with ethyl acetate (3×75 ml). The combined organic phases was dried with sodium sulfate and evaporated to dryness. Yield 8.2 g (69%) of (5), mp 94.5-96.5° C., $[\alpha]_D^{25}=+67°$.

(+)-Cis-1-methyl-3-hydroxymethyl-4-(3,4-dichlorophenyl)-piperidine fumarate salt, mp 147-149° C., $[\alpha]_D^{25}=+68°$.

Procedure (b)

(−)-Cis-1-methyl-3-hydroxymethyl-4-(3,4-dichlorophenyl)-piperidine (6)

The toluene from the recrystallisation mentioned under procedure (a) was added water (75 ml) and concentrated ammonia (aq) until basic pH. The mixture was extracted with ethyl acetate (2×75 ml). The combined organic phases was dried with sodium sulfate and evaporated to dryness. The residue was dissolved in absolute ethanol (60 ml) and (+) mandelic acid (6.6 g, 43.4 mmol) was added.

The procedure now follows the procedure mentioned under procedure (a) yielding 7.4 g (62%) of (6), mp 95-97° C., $[\alpha]_D^{25}=-65°$.

(−)-Cis-1-methyl-3-hydroxymethyl-4-(3,4-dichlorophenyl)-piperidine fumarate salt, mp 148-150° C., $[\alpha]_D^{25}=-67°$.

Method A2

The pure enantiomers, (+)- and (−)-Trans-1-methyl-3-hydroxymethyl-4-(3,4-dichlorophenyl)-piperidine, can be made by isomerisation of (5) and (6).

(+)-Trans-1-methyl-3-hydroxymethyl-4-(3,4-dichlorophenyl)-piperidine (7)

A solution of (5) (10.0 g, 36 mmol) and potassium tert-butoxide (12.0 g, 1.08 mmol) in dimethylformamide (75 ml) was stirred over night. CaCl$_2$ (75 ml, 3M) was added and the reaction mixture was extracted with ethyl acetate (2×200 ml). The combined organic phases was dried with sodium sulfate and evaporated to dryness. The residue was recrystallized from ethyl acetate (7 ml). Yield 6.3 g (63%) of (7), mp 137-139° C., $[\alpha]_D^{25}=+39°$.

(−)-Trans-1-methyl-3-hydroxymethyl-4-(3,4-dichlorophenyl)-piperidine (8)

(8) was synthesized from (6) (2.0 g, 7.3 mmol) according to method (A2) giving 1.4 g (70%) of (8), mp 137-139° C., $[\alpha]_D^{25}=-38°$.

(−)-Trans-1-methyl-3-hydroxymethyl-4-(3,4-dichlorophenyl)-piperidine fumarate salt, mp 138-140° C., $[\alpha]_D^{25}=-25°$.

Example 3

Method B1

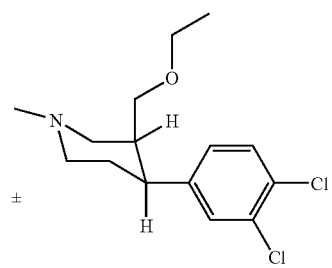

(±)-Cis-1-methyl-3-ethoxymethyl-4-(3,4-dichlorophenyl)-piperidine (9)

A solution of (3) (2.4 g, 8.6 mmol) in tetrahydrofuran (40 ml) was added 60% NaH (0.69 g, 17 mmol) and stirred at room temperature for one hour. Diethyl sulfate (1.4 ml, 11 mmol) was added and the reaction mixture stirred over night. Water was added and the reaction mixture was extracted with diethyl ether (3×40 ml). The combined organic phases was dried with magnesium sulfate and evaporated to dryness. Column chromatography, using a mixture of dichloromethane, methanol and ammonia (aq) (9:1:1%) yielded 1.5 g (56%) of product (9) (oil).

Likewise was made:
(±)-Cis-1-methyl-3-methoxymethyl-4-(3,4-dichlorophenyl)-piperidine (10) by methylation of (3) with dimethyl sulfate (oil).

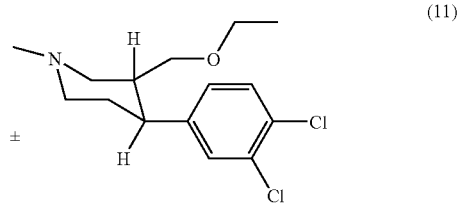

(±)-Trans-1-methyl-3-ethoxymethyl-4-(3,4-dichlorophenyl)-piperidine (11)

(11) was synthesized from (4) (1.8 g, 6.6 mmol) according to method (B1) giving 0.83 g (43%) of product (11) (oil).

Likewise was made:
(±)-Trans-1-methyl-3-methoxymethyl-4-(3,4-dichlorophenyl)-piperidine (12) by methylation of (4) with dimethyl sulfate (oil).

Method B2

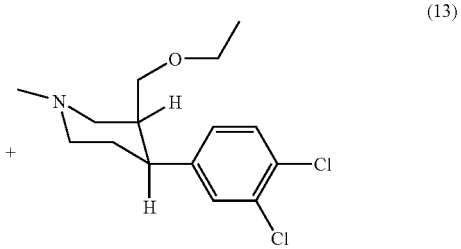

(+)-Cis-1-methyl-3-ethoxymethyl-4-(3,4-dichlorophenyl)-piperidine fumarate salt (13)

To a solution of (5) (11.0 g, 40 mmol) in tetrahydrofuran (150 ml) was added potassium tert-butoxide (13.3 g, 120 mmol). The reaction mixture was stirred for one hour and cooled to 5° C. Diethyl sulfate (5.7 ml, 44 mmol) was added and the reaction mixture stirred over night. Saturated sodium chloride (150 ml) and water (50 ml) were added and the reaction mixture was extracted with ethyl acetate (2×80 ml), dried with sodium sulfate and evaporated to dryness. Yield 129 (99%) of (13). Mp 72.5-74° C. $[\alpha]_D^{25}=+65°$.

Like wise was made:
(+)-Cis-1-methyl-3-methoxymethyl-4-(3,4-dichlorophenyl)-piperidine (14) by alkylation of (5) with dimethyl sulfate (oil).
(−)-Cis-1-methyl-3-methoxymethyl-4-(3,4-dichlorophenyl)-piperidine (15) by alkylation of (6) with dimethyl sulfate (oil).
(+)-Cis-1-methyl-3-cyclopropylmethoxymethyl-4-(3,4-dichlorophenyl)-piperidine fumarate salt (16) by alkylation of (5) with (bromomethyl)cyclopropane. Mp 187-188.5° C., $[\alpha]_D^{25}=+63°$.
(−)-Cis-1-methyl-3-cyclopropylmethoxymethyl-4-(3,4-dichlorophenyl)-piperidine fumarate salt (17) by alkylation of (6) with (bromomethyl)cyclopropane. Mp 184.5-187.6° C., $[\alpha]_D^{25}=-66°$.
(−)-Cis-1-methyl-3-isobutoxymethyl-4-(3,4-dichlorophenyl)-piperidine fumarate salt (18) by alkylation of (6) with 1-bromo-2-methylpropane. Mp 181-183° C., $[\alpha]_D^{25}=-64°$.
(+)-Trans-1-methyl-3-ethoxymethyl-4-(3,4-dichlorophenyl)-piperidine (19) by alkylation of (7) with diethyl sulfate (oil).
(−)-Trans-1-methyl-3-ethoxymethyl-4-(3,4-dichlorophenyl)-piperidine (20) by alkylation of (8) with diethyl sulfate (oil).
(+)-Trans-1-methyl-3-methoxymethyl-4-(3,4-dichlorophenyl)-piperidine (21) by alkylation of (7) with dimethyl sulfate, (oil), $[\alpha]2=+44°$.
(−)-Trans-1-methyl-3-methoxymethyl-4-(3,4-dichlorophenyl)-piperidine fumarate salt (22) by alkylation of (8) with dimethyl sulfate. Mp. 50-70° C. (hygroscopic), $[\alpha]_D^{25}=-23°$.
(−)-Trans-1-methyl-3-cyclopropylmethoxymethyl-4-(3,4-dichlorophenyl)-piperidine fumarate salt (23) by alkylation of (8) with (bromomethyl)cyclopropane. Mp 180-182° C., $[\alpha]_D^{25}=-31°$.
(−)-Trans-1-methyl-3-isobutoxymethyl-4-(3,4-dichlorophenyl)-piperidine fumarate salt (24) by alkylation of (8) with 1-bromo-2-methylpropane. Mp 162-164° C., $[\alpha]_D^{25}=-29°$.

Likewise is made:
(+)-Cis-1-methyl-3-isobutoxymethyl-4-(3,4-dichlorophenyl)-piperidine fumarate salt
(+)-Trans-1-methyl-3-isobutoxymethyl-4-(3,4-dichlorophenyl)-piperidine fumarate salt
(+)-Trans-1-methyl-3-cyclopropylmethoxymethyl-4-(3,4-dichlorophenyl)-piperidine fumarate salt Example 4

Method C

The racemate of (±)-Cis-1-methyl-3-ethoxymethyl-4-(3,4-dichlorophenyl)-piperidine (9) can be separated into the individual enantiomers by the dibenzoyltartrate salts.

Procedure (a)

(+)-Cis-1-methyl-3-ethoxymethyl-4-(3,4-dichlorophenyl)-piperidine hydrobromide (13)

(±)-Cis-1-methyl-3-ethoxymethyl-4-(3,4-dichlorophenyl)-piperidine (9) (1.1 g, 3.7 mmol) and (−)-dibenzoyltartaric acid (0.48 g, 1.3 mmol) were dissolved in 99% ethanol (10 ml) and evaporated to dryness. The evaporation residue was crystallized from toluene (3 ml). Recrystallized from a mixture of toluene (10 ml) and ethanol (10 ml). The precipitate was isolated and dissolved in a mixture of 4 N NaOH (5 ml) and diethyl ether (10 ml). The diethyl ether was separated and dried with magnesium sulfate yielding 0.25 g (45%) of the product as the free base. Hydrobromic acid (0.20 ml, 1.7 mmol) was added and the mixture evaporated to dryness. The residue was recrystallized from ethanol (2 ml) and diethyl ether (10 ml) to yield 0.20 g (28%) of (13), mp 183-185° C., $[\alpha]_D^{25}=+62.8°$, (c=14 mg/ml in 99% ethanol).

Procedure (b)

(−)-Cis-1-methyl-3-ethoxymethyl-4-(3,4-dichlorophenyl)-piperidine hydrobromide (25)

The toluene from the recrystallization mentioned under procedure (a) was added 4 N NaOH (5 ml) and extracted with diethyl ether (3×25 ml), dried with magnesium sulfate and evaporated to dryness. The residue was dissolved in 99% ethanol (10 ml) and (+)dibenzoyltartaric acid (0.67 g, 1.8 mmol) added. The procedure now follows the procedure mentioned under (a) yielding 0.14 g (20%) of (25), mp 183-185° C., $[\alpha]_D^{25}=-66.1°$, (c=14 mg/ml in 99% ethanol).

(+)-Trans-1-methyl-3-ethoxymethyl-4-(3,4-dichlorophenyl)-piperidine hydrobromide (19) and (−)-Trans-1-methyl-3-ethoxymethyl-4-(3,4-dichlorophenyl)-piperidine hydrobromide (20)

(19) and (20) were resolved from (11) (0.83 g, 2.8 mmol) according to the procedure used in method C yielding 0.16 g (30%) of (19), mp 222°-224° C., $[\alpha]_D^{25}=+34.9°$ (c=10 mg/ml in 99% ethanol); and 0.14 g (26%) of (20), mp 219°-221° C., $[\alpha]_D^{25}=-32.7°$ (c=10 mg/ml in 99% ethanol).

(+)-Cis-1-methyl-3-methoxymethyl-4-(3,4-dichlorophenyl)-piperidine hydrobromide (14) and (−)-Cis-1-methyl-3-methoxymethyl(3,4-dichlorophenyl)-piperidine hydrobromide (15)

(14) and (15) were resolved from (10) according to the procedure in method C. $[\alpha]_D^{25}=+65°$, mp 212-215° C. for (14) and $[\alpha]_D^{25}=-65°$, mp 212-215° C. for (15).

Example 5

(+)-Cis-3-ethoxymethyl-4-(3,4-dichlorophenyl)-piperidine (26)

A mixture of (13) 0.70 g and 1-chloroethylchloroformate (2.5 ml) was stirred at 100° C. for 2 days where after 4 N NaOH (25 ml) was added. The mixture was stirred with reflux overnight. After cooling, the mixture was extracted with toluene. The organic phase was dried and evaporated to give an oil which was subjected to column chromatography ($SiO_2$, methylene chloride, MeOH, ammonia 9:1:1%) to give the product as pale crystals. Mp 68-70° C.

(+)-Cis-3-ethoxymethyl-4-(3,4-dichlorophenyl)-piperidine fumarate salt, mp 149-151° C. $[\alpha]_D^{25}=+68°$.

Likewise was made:
(−)-Cis-3-ethoxymethyl-4-(3,4-dichlorophenyl)-piperidine hydrobromide (27), mp. 182-184° C., $[\alpha]_D^{25}=-75°$.
(+)-Cis-3-methoxymethyl-4-(3,4-dichlorophenyl)-piperidine fumarate salt (28), mp 154.5-156° C., $[\alpha]_D^{25}=+66°$.
(−)-Cis-3-methoxymethyl-4-(3,4-dichlorophenyl)-piperidine fumarate salt (29), mp 147-149° C., $[\alpha]_D^{25}=-68°$.
(+)-Cis-3-cyclopropylmethoxymethyl-4-(3,4-dichlorophenyl)-piperidine fumarate salt
(30), mp 172-173.5° C., $[\alpha]_D^{25}=+63°$.
(−)-Cis-3-cyclopropylmethoxymethyl-4-(3,4-dichlorophenyl)-piperidine fumarate salt (31), mp 175-176.5° C., $[\alpha]_D^{25}=-65°$.
(+)-Trans-3-ethoxymethyl-4-(3,4-dichlorophenyl)-piperidine (32), (Oil), $[\alpha]_D^{25}=+46°$.
(−)-Trans-3-ethoxymethyl-4-(3,4-dichlorophenyl)-piperidine fumarate salt (33), mp. 140-142° C., $[\alpha]_D^{25}=-37°$.
(+)-Trans-3-methoxymethyl-4-(3,4-dichlorophenyl)-piperidine (34), (Oil), $[\alpha]^{25}=+44°$.
(−)-Trans-3-methoxymethyl-4-(3,4-dichlorophenyl)-piperidine fumarate salt (35), mp 140-142° C., $[\alpha]_D^{25}=-31°$.
(−)-Trans-3-cyclopropylmethoxymethyl-4-(3,4-dichlorophenyl)-piperidine fumarate salt (36), mp 153.5-155.5° C., $[\alpha]_D^{25}=-37°$.

Likewise is made,
(+)-Trans-3-cyclopropylmethoxymethyl-(3,4-dichlorophenyl)-piperidine fumarate salt
(+)-Cis-3-isobutoxymethyl-4-(3,4-dichlorophenyl)-piperidine fumarate salt
(−)-Cis-3-isobutoxymethyl-4-(3,4-dichlorophenyl)-piperidine fumarate salt
(+)-Trans-3-isobutoxymethyl-(3,4-dichlorophenyl)-piperidine fumarate salt
(−)-Trans-3-isobutoxymethyl-4-(3,4-dichlorophenyl)-piperidine fumarate salt

What is claimed is:

1. A piperidine compound of the Formula I:

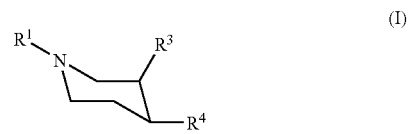

or any of its isomers or any mixture of its isomers, or a pharmaceutically acceptable salt thereof,
wherein
$R^1$ represents hydrogen or alkyl;
$R^3$ represents —$CH_2$—O—$R^c$;
wherein $R^c$ represents alkyl or cycloalkylalkyl;
$R^4$ represents

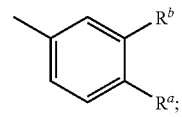

wherein $R^a$ and $R^b$ independently of each other represent halo.

2. The chemical compound of claim 1, or any of its isomers or any mixture of its isomers, or a pharmaceutically acceptable salt thereof, wherein
$R^1$ represents hydrogen.

3. The chemical compound of claim 1, or any of its isomers or any mixture of its isomers, or a pharmaceutically acceptable salt thereof, wherein
$R^1$ represents alkyl.

4. The chemical compound according to claim 1, or any of its isomers or any mixture of its isomers, or a pharmaceutically acceptable salt thereof, wherein $R^c$ represents alkyl.

5. The chemical compound according to claim 1, or any of its isomers or any mixture of its isomers, or a pharmaceutically acceptable salt thereof, wherein $R^c$ represents cycloalkylalkyl.

6. The chemical compound according to claim 1, or any of its isomers or any mixture of its isomers, or a pharmaceutically acceptable salt thereof, wherein $R^a$ represents chloro and $R^b$ represents chloro.

7. The chemical compound of claim 1, which is
1-methyl-3-ethoxymethyl-4-(3,4-dichlorophenyl)-piperidine;
1-methyl-3-methoxymethyl-4-(3,4-dichlorophenyl)-piperidine;
1-methyl-3-cyclopropylmethoxymethyl-4-(3,4-dichlorophenyl)-piperidine;
1-methyl-3-isobutoxymethyl-4-(3,4-dichlorophenyl)-piperidine;
3-ethoxymethyl-4-(3,4-dichlorophenyl)-piperidine;
3-methoxymethyl-4-(3,4-dichlorophenyl)-piperidine;
3-cyclopropylmethoxymethyl-4-(3,4-dichlorophenyl)-piperidine;
or any of its isomers or any mixture of its isomers, or a pharmaceutically acceptable salt thereof.

8. The chemical compound of claim 1, which is
(±)-Cis-1-methyl-3-ethoxymethyl-4-(3,4-dichlorophenyl)-piperidine;
(±)-Cis-1-methyl-3-methoxymethyl-4-(3,4-dichlorophenyl)-piperidine;
(±)-Trans-1-methyl-3-ethoxymethyl-4-(3,4-dichlorophenyl)-piperidine;
(±)-Trans-1-methyl-3-methoxymethyl-4-(3,4-dichlorophenyl)-piperidine;
(+)-Cis-1-methyl-3-ethoxymethyl-4-(3,4-dichlorophenyl)-piperidine;
(+)-Cis-1-methyl-3-methoxymethyl-4-(3,4-dichlorophenyl)-piperidine;
(−)-Cis-1-methyl-3-methoxymethyl-4-(3,4-dichlorophenyl)-piperidine;
(+)-Cis-1-methyl-3-cyclopropylmethoxymethyl-4-(3,4-dichlorophenyl)-piperidine;
(−)-Cis-1-methyl-3-cyclopropylmethoxymethyl-4-(3,4-dichlorophenyl)-piperidine;
(−)-Cis-1-methyl-3-isobutoxymethyl-4-(3,4-dichlorophenyl)-piperidine;
(+)-Trans-1-methyl-3-ethoxymethyl-4-(3,4-dichlorophenyl)-piperidine;
(−)-Trans-1-methyl-3-ethoxymethyl-4-(3,4-dichlorophenyl)-piperidine;
(+)-Trans-1-methyl-3-methoxymethyl-4-(3,4-dichlorophenyl)-piperidine;
(−)-Trans-1-methyl-3-methoxymethyl-4-(3,4-dichlorophenyl)-piperidine;
(−)-Trans-1-methyl-3-cyclopropylmethoxymethyl-4-(3,4-dichlorophenyl)-piperidine;
(−)-Trans-1-methyl-3-isobutoxymethyl-4-(3,4-dichlorophenyl)-piperidine;
(+)-Cis-1-methyl-3-isobutoxymethyl-4-(3,4-dichlorophenyl)-piperidine;
(+)-Trans-1-methyl-3-isobutoxymethyl-4-(3,4-dichlorophenyl)-piperidine;
(+)-Trans-1-methyl-3-cyclopropylmethoxymethyl-4-(3,4-dichlorophenyl)-piperidine;
(−)-Cis-1-methyl-3-ethoxymethyl-4-(3,4-dichlorophenyl)-piperidine;
(+)-Cis-3-ethoxymethyl-4-(3,4-dichlorophenyl)-piperidine;
(−)-Cis-3-ethoxymethyl-4-(3,4-dichlorophenyl)-piperidine;
(+)-Cis-3-methoxymethyl-4-(3,4-dichlorophenyl)-piperidine;
(−)-Cis-3-methoxymethyl-4-(3,4-dichlorophenyl)-piperidine;
(+)-Cis-3-cyclopropylmethoxymethyl-4-(3,4-dichlorophenyl)-piperidine;
(−)-Cis-3-cyclopropylmethoxymethyl-4-(3,4-dichlorophenyl)-piperidine;
(+)-Trans-3-ethoxymethyl-4-(3,4-dichlorophenyl)-piperidine;
(−)-Trans-3-ethoxymethyl-4-(3,4-dichlorophenyl)-piperidine;
(+)-Trans-3-methoxymethyl-4-(3,4-dichlorophenyl)-piperidine;
(−)-Trans-3-methoxymethyl-4-(3,4-dichlorophenyl)-piperidine;
(−)-Trans-3-cyclopropylmethoxymethyl-4-(3,4-dichlorophenyl)-piperidine;
(+)-Trans-3-cyclopropylmethoxymethyl-4-(3,4-dichlorophenyl)-piperidine;
(+)-Cis-3-isobutoxymethyl-4-(3,4-dichlorophenyl)-piperidine;
(−)-Cis-3-isobutoxymethyl-4-(3,4-dichlorophenyl)-piperidine;
(+)-Trans-3-isobutoxymethyl-4-(3,4-dichlorophenyl)-piperidine;
(−)-Trans-3-isobutoxymethyl-4-(3,4-dichlorophenyl)-piperidine;
or a pharmaceutically acceptable salt thereof.

* * * * *